(12) United States Patent
Johnson

(10) Patent No.: US 11,602,392 B2
(45) Date of Patent: Mar. 14, 2023

(54) SURGICAL INSTRUMENTS AND SYSTEMS INCORPORATING MACHINE LEARNING BASED TISSUE IDENTIFICATION AND METHODS THEREOF

(71) Applicant: Covidien LP, Mansfield, MA (US)

(72) Inventor: Joshua H. Johnson, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 295 days.

(21) Appl. No.: 17/032,133

(22) Filed: Sep. 25, 2020

(65) Prior Publication Data

US 2021/0007795 A1 Jan. 14, 2021

Related U.S. Application Data

(62) Division of application No. 15/444,422, filed on Feb. 28, 2017, now Pat. No. 10,786,298.

(Continued)

(51) Int. Cl.
*A61B 18/14* (2006.01)
*G16H 50/20* (2018.01)
*A61B 18/00* (2006.01)

(52) U.S. Cl.
CPC ......... *A61B 18/1445* (2013.01); *G16H 50/20* (2018.01); *A61B 18/1442* (2013.01); *A61B 2018/00636* (2013.01); *A61B 2018/00642* (2013.01); *A61B 2018/00648* (2013.01); *A61B 2018/00702* (2013.01);
(Continued)

(58) Field of Classification Search
CPC ........... A61B 2018/00636; A61B 2018/00642; A61B 2018/00648; A61B 2018/00702; A61B 2018/00708; A61B 2018/00773; A61B 2018/00779; A61B 2018/00875; A61B 2018/00898; A61B 2018/00904; A61B 18/1442; A61B 18/1445; A61B 18/1447; A61B 2018/145; A61B 2018/1452; A61B 2018/1455; A61B 2018/1457; G16H 50/20; G06F 19/30
See application file for complete search history.

(56) References Cited

U.S. PATENT DOCUMENTS 5,558,671 A 9/1996 Yates
7,720,267 B2 5/2010 Fuchs et al.
(Continued)

FOREIGN PATENT DOCUMENTS

WO 2014140085 A1 9/2014

*Primary Examiner* — Ronald Hupczey, Jr.
*Assistant Examiner* — Bradford C. Blaise
(74) *Attorney, Agent, or Firm* — Carter, DeLuca & Farrell, LLP

(57) ABSTRACT

A surgical system includes an end effector assembly having first and second jaw members, a generator, and one or more machine learning applications. The first and/or second jaw member is movable relative to the other from a spaced-apart position to an approximated position for grasping tissue therebetween. The jaw members are configured to conduct energy therebetween and through tissue grasped therebetween. The generator includes an energy output configured to supply energy to the jaw members, a main controller configured to control the energy output, and sensor circuitry configured to sense impedance and/or power. The machine learning application(s) is configured to determine a type of tissue grasped between the first and second jaw members based upon the impedance and/or power sensed by the sensor circuitry.

19 Claims, 4 Drawing Sheets

Related U.S. Application Data

(60) Provisional application No. 62/301,870, filed on Mar. 1, 2016.

(52) U.S. Cl.
CPC ............... *A61B 2018/00708* (2013.01); *A61B 2018/00773* (2013.01); *A61B 2018/00779* (2013.01); *A61B 2018/00875* (2013.01); *A61B 2018/00898* (2013.01); *A61B 2018/00904* (2013.01)

(56) References Cited

U.S. PATENT DOCUMENTS

| | | |
|---|---|---|
| 8,034,049 B2 | 10/2011 | Odom et al. |
| 8,831,327 B2 | 9/2014 | Santamaria-Pang et al. |
| 8,864,761 B2 | 10/2014 | Johnson |
| 10,786,298 B2 | 9/2020 | Johnson |
| 2002/0072686 A1 | 6/2002 | Hoey |
| 2006/0036372 A1 | 2/2006 | Yener et al. |
| 2007/0173803 A1 | 7/2007 | Wham et al. |
| 2007/0173805 A1 | 7/2007 | Weinberg et al. |
| 2007/0276245 A1 | 11/2007 | Konofagou |
| 2008/0281316 A1 | 11/2008 | Carlton et al. |
| 2009/0298703 A1 | 12/2009 | Gough et al. |
| 2011/0071521 A1 | 3/2011 | Gilbert |
| 2012/0283731 A1 | 11/2012 | Unger et al. |
| 2013/0041367 A1 | 2/2013 | Wham et al. |
| 2017/0007308 A1 | 1/2017 | Mun | ized, and/or seal, tissue.
SURGICAL INSTRUMENTS AND SYSTEMS INCORPORATING MACHINE LEARNING BASED TISSUE IDENTIFICATION AND METHODS THEREOF

CROSS REFERENCE TO RELATED APPLICATION

The present application is a divisional of U.S. patent application Ser. No. 15/444,422, filed Feb. 28, 2017, now U.S. Pat. No. 10,786,298, which claims the benefit of and priority to U.S. Provisional Patent Application Ser. No. 62/301,870, filed on Mar. 1, 2016. The entire contents of each of the foregoing applications are hereby incorporated herein by reference

BACKGROUND

Technical Field

The present disclosure relates to surgical instruments and systems and, more particularly, to surgical instruments, systems, and methods incorporating machine learning based tissue identification.

Background of Related Art

Surgical instruments are utilized to perform various functions on tissue structures. A surgical forceps, for example, is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue.

While surgical instruments such as energy-based surgical forceps are effective at treating tissue, it is often left up to the surgeon to properly position the instrument for use and to ensure that only appropriate tissue structure(s) are treated. For example, with respect to energy-based surgical forceps, it is often desirable to treat vessels, vascular tissue, and the like, while avoiding other tissue structures such as nerves. Surgeons must typically rely on experience, visualization of the surgical field, and/or "feel" in order to distinguish tissue to be treated from that to be avoided.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A surgical system provided in accordance with aspects of the present disclosure includes a surgical instrument, a generator, and one or more machine learning applications. The surgical instrument includes an end effector assembly having first and second jaw members. One or both of the jaw members is movable relative to the other from a spaced-apart position to an approximated position for grasping tissue therebetween. The jaw members include electrically-conductive plates configured to conduct energy therebetween and through tissue grasped between the first and second jaw members. First and second electrical leads are coupled to the electrically-conductive plates of the first and second jaw members, respectively. The generator includes an energy output configured to supply energy to the electrically-conductive plates of the first and second jaw members via the first and second electrical leads. The generator further includes a main controller configured to control the energy output and sensor circuitry electrically coupled to the first and second electrical leads and configured to sense impedance and/or power during the conduction of energy between the electrically-conductive plates and through tissue grasped between the first and second jaw members. The machine learning application(s) is configured to determine a type of tissue grasped between the first and second jaw members based upon the impedance and/or power sensed by the sensor circuitry.

In an aspect of the present disclosure, the machine learning application(s) is stored within the generator. Alternatively, the machine learning application(s) may be stored remotely from the generator.

In another aspect of the present disclosure, the machine learning application(s) is trained using experimental data and/or previous procedure data.

In yet another aspect of the present disclosure, the machine learning application(s) is configured to communicate the determined tissue type to the main controller. In such aspects, in response to receiving the determined tissue type, the main controller is configured to determine whether the determined tissue type is acceptable for tissue treatment or not acceptable for tissue treatment.

In still another aspect of the present disclosure, if the determined tissue type is determined not to be acceptable for tissue treatment, the main controller is further configured to inhibit further supply of energy to the electrically-conductive plates and/or output a warning. In aspects, the warning is capable of being manually overridden.

In still yet another aspect of the present disclosure, if the determined tissue type is determined to be acceptable for tissue treatment, the main controller is further configured to control the supply of energy to the electrically-conductive plates to complete tissue treatment.

In another aspect of the present disclosure, the main controller is configured to determine whether the determined tissue type is acceptable for tissue treatment or not acceptable for tissue treatment during an initial stage of tissue treatment prior to permanently damaging tissue. This initial stage may be during the initial 250 ms of tissue treatment.

In still another aspect of the present disclosure, the machine learning application(s) includes a Support Vector Machine (SVM), implements Principle Component Analysis, implements a Hidden Markov Model (HMM), and/or employs the Monte Carlo Method.

In yet another aspect of the present disclosure, the machine learning application(s) utilizes data representative of a snapshot in time of impedance and/or power during the conduction of energy between the electrically-conductive plates and through tissue grasped between the first and second jaw members to determine the tissue type.

In still yet another aspect of the present disclosure, the machine learning application(s) utilizes data representative of impedance and/or power over an elapsed time during the conduction of energy between the electrically-conductive plates and through tissue grasped between the first and second jaw members to determine the tissue type.

A method of surgery provided in accordance with aspects of the present disclosure includes grasping tissue, conducting energy through the grasped tissue, sensing impedance and/or power during the conduction of energy through the grasped tissue, and running one or more machine learning application(s) to determine a type of the grasped tissue based upon the sensed impedance and/or sensed power.

In an aspect of the present disclosure, the method further includes determining whether the determined type of the grasped tissue is acceptable for tissue treatment or is not acceptable for tissue treatment. In such aspects, if it is determined that the determined type of grasped tissue is acceptable for tissue treatment, the method further includes continuing to conduct energy through the grasped tissue to complete tissue treatment. On the other hand, if it is determined that the determined type of grasped tissue is not acceptable for tissue treatment, the method further includes stopping the conduction of energy through the grasped tissue and/or outputting a warning.

In another aspect of the present disclosure, determining whether the determined type of the grasped tissue is acceptable for tissue treatment or is not acceptable for tissue treatment is performed during an initial 250 ms of the conduction of energy through the grasped tissue.

In still yet another aspect of the present disclosure, the type of the grasped tissue is determined by the one or more machine learning application(s) based upon a snapshot in time of impedance and/or power during the conduction of energy through the grasped tissue or based upon impedance and/or power over an elapsed time during the conduction of energy through the grasped tissue.

BRIEF DESCRIPTION OF THE DRAWINGS

Various aspects and features of the present disclosure are described herein with reference to the drawings wherein.

DETAILED DESCRIPTION

Figure 1:
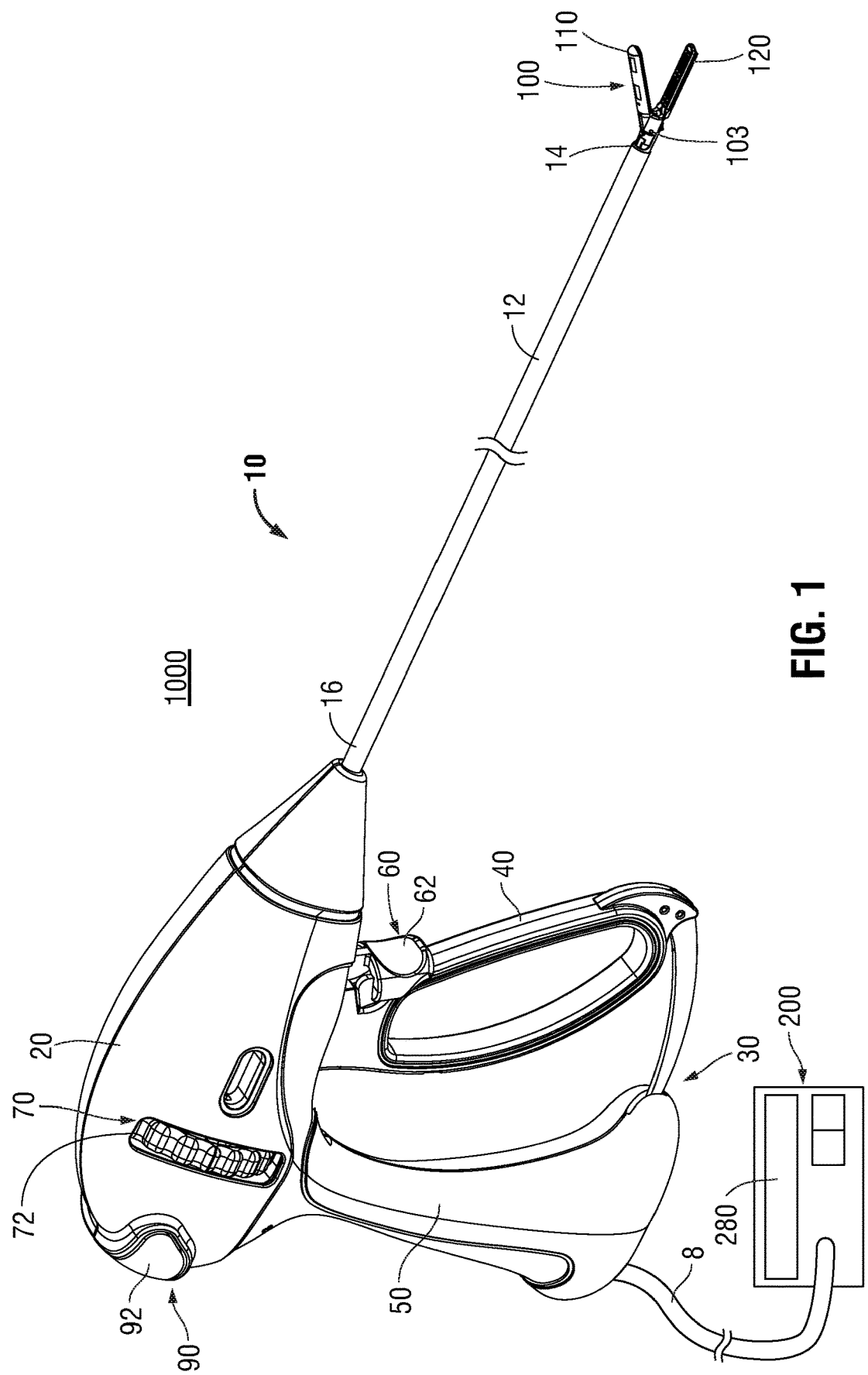
FIG. 1 is a perspective view of a surgical system provided in accordance with the present disclosure including an energy-based surgical instrument and a generator.

Turning to FIG. 1, a surgical system provided in accordance with the present disclosure is shown generally identified by reference numeral 1000. Surgical system 1000 includes an energy-based surgical instrument, e.g., an electrosurgical forceps 10, coupled to a generator 200. Forceps 10 is configured to grasp and treat tissue and may be utilized in connection with open and/or endoscopic surgical procedures; however, it is contemplated that any other suitable energy-based surgical instrument may be utilized as an alternative or in addition to forceps 10 as part of surgical system 1000. Obviously, different electrical and mechanical connections and considerations apply to each particular type of instrument; however, the aspects and features of the present disclosure remain generally consistent regardless of the particular instrument(s) used. As detailed below, surgical system 1000 is configured to incorporate machine learning to facilitate the treatment of tissue by enabling the determination of a type of tissue being treated, thus helping to ensure that only appropriate tissue structure(s), e.g., vessels and vascular tissue, are treated and that tissue structure(s) not to be treated, e.g., nerves, are avoided. As utilized herein, tissue type may refer to a specific tissue, e.g., organ tissue; a positively-defined category of tissue, e.g., vascular tissue; a negatively-defined category of tissue, e.g., nerveless tissue (or tissue with minimal nerve structures); a parameter-based tissue grouping, e.g., tissue associated with a particular sensed parameter; and/or a similarity-based tissue grouping, e.g., separating tissue into "A" and "B" groups based upon similarities and differences.

For the purposes herein, forceps 10 is generally described. Forceps 10 includes a housing 20, a handle assembly 30, a trigger assembly 60, a rotating assembly 70, an activation assembly 90, and an end effector assembly 100. Forceps 10 further includes a shaft 12 having a distal end 14 configured to mechanically engage end effector assembly 100 and a proximal end 16 that mechanically engages housing 20. A cable 8 connects forceps 10 to generator 200 although forceps 10 may alternatively be configured to wirelessly couple to generator 200. As will be detailed below, cable 8 houses a plurality of electrical leads including electrical leads 9a, 9b (shown schematically in FIG. 2B) that extend through forceps 10 to couple generator 200 to end effector assembly 100 of forceps 10. Activation assembly 90 includes an activation switch 92 provided on housing 20 that may be configured as an on/off switch for selectively activating and deactivating forceps 10. More specifically, activation switch 92 is selectively activatable to supply energy to jaw members 110, 120 of end effector assembly 100 to treat tissue grasped therebetween.

Handle assembly 30 includes a fixed handle 50 and a movable handle 40. Fixed handle 50 is integrally associated with housing 20 and movable handle 40 is movable relative to fixed handle 50. Movable handle 40 of handle assembly 30 is operably coupled to a drive assembly (not shown) that, together, mechanically cooperate to impart movement of jaw members 110, 120 of end effector assembly 100 between a spaced-apart position and an approximated position to grasp tissue therebetween. More specifically, movable handle 40 is initially spaced-apart from fixed handle 50 and, correspondingly, jaw members 110, 120 are disposed in the spaced-apart position. Movable handle 40 is movable from this initial position to a compressed position corresponding to the approximated position of jaw members 110, 120. Rotating assembly 70 includes a rotation wheel 72 that is rotatable in either direction to correspondingly rotate end effector assembly 100 relative to housing 20.

Figure 2:
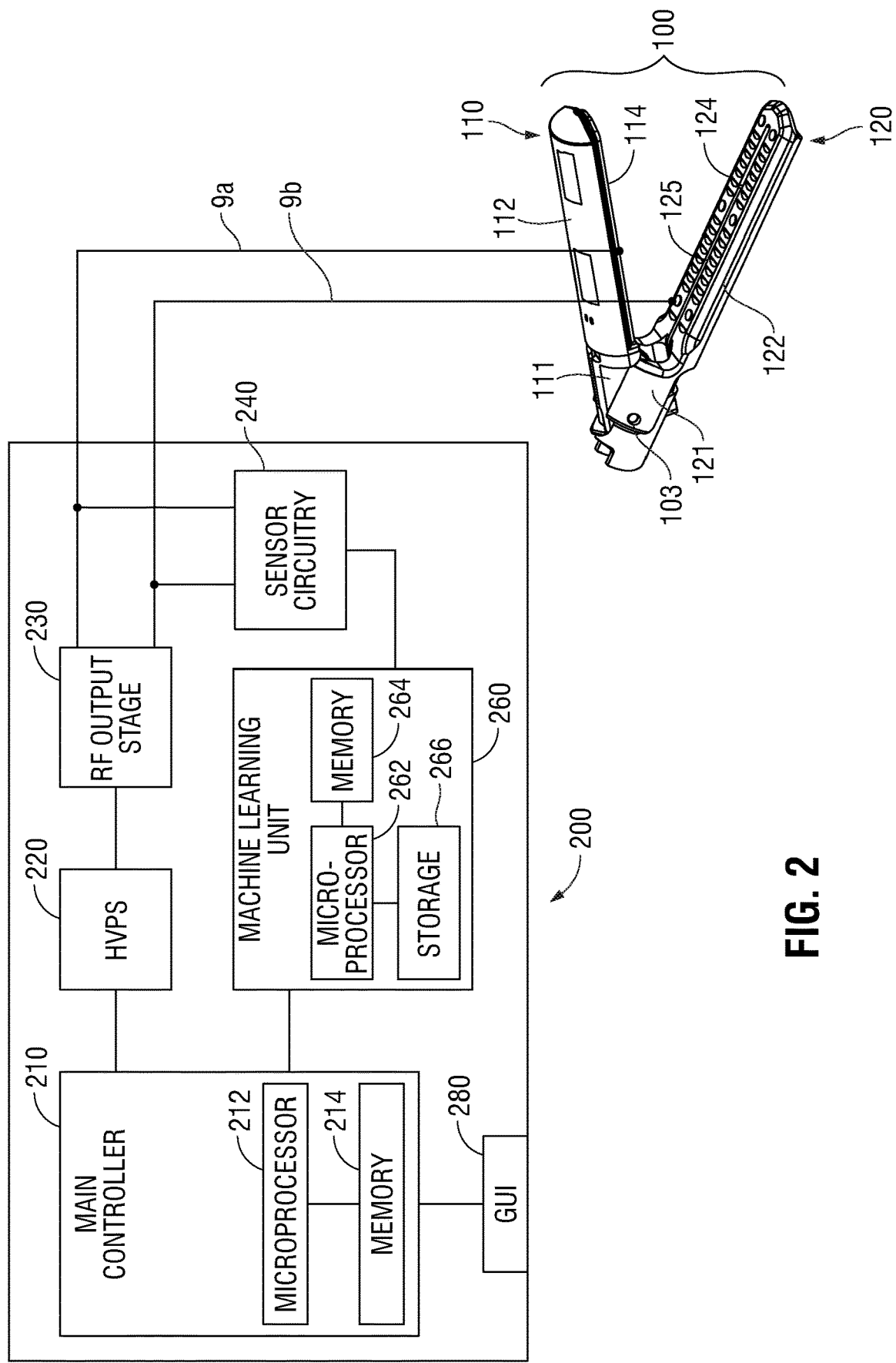
FIG. 2 is a schematic illustration of the end effector assembly of the energy-based surgical instrument of FIG. 1 and the generator of FIG. 1.

With additional reference to FIG. 2, end effector assembly 100 of forceps 10 includes a pair of jaw members 110, 120. Each jaw member 110, 120 of end effector assembly 100 includes a proximal flange portion 111, 121, an outer insulative jaw housing 112, 122, and a tissue-contacting plate 114, 124, respectively. Proximal flange portions 111, 121 of jaw members 110, 120 are pivotably coupled to one another about pivot 103 to permit pivoting of one or both of jaw members 110, 120 between the spaced-apart and approximated positions. One or both of proximal flange portions 111, 121 of jaw members 110, 120 is also coupled to a drive bar of the drive assembly (not shown), which is slidably disposed within shaft 12 and configured to reciprocate therethrough to effect pivoting of jaw members 110, 120 between the spaced-apart and approximated positions.

Tissue-contacting plates 114, 124 of jaw members 110, 120 are formed from an electrically-conductive material, e.g., for conducting energy therebetween to treat tissue. Although detailed herein as conducting electrosurgical energy, tissue-contacting plates 114, 124 may alternatively be configured to conduct any suitable energy through tissue grasped therebetween for energy-based tissue treatment.

Tissue-contacting plates 114, 124 are coupled to activation switch 92 and generator 200, e.g., via electrical leads 9a and 9b, respectively, such that electrosurgical energy may be selectively supplied to tissue-contacting plate 114 and/or tissue-contacting plate 124 and conducted therebetween and through tissue disposed between jaw members 110, 120 to treat tissue. Electrical leads 9a and 9b and tissue-contacting plates 114, 124 also cooperate with sensor circuitry 240 of generator 200 to allow for sensing of various parameters of tissue grasped between jaw members 110, 120 and/or the energy being conducted therebetween. Parameters such as tissue impedance and power are advantageous in that additional sensors and/or other components in end effector assembly 100 are not required; rather, such parameters can be sensed at generator 200, e.g., via electrical leads 9a and 9b.

In some embodiments, a knife assembly (not shown) is disposed within shaft 12 and a knife channel 125 (only knife channel 125 of jaw member 120 is shown) is defined within one or both jaw members 110, 120 to permit reciprocation of a knife of the knife assembly therethrough, e.g., upon actuation of trigger 62 of trigger assembly 60. In use, once jaw members 110, 120 have been pivoted from the spaced-apart position to the approximated position to grasp tissue therebetween, and, if desired, after tissue treatment, the knife may be advanced from a retracted position to an extended position, e.g., via activation of trigger 62, such that the knife is translated through knife channels 125 of jaw members 110, 120, respectively, to cut tissue grasped therebetween.

Continuing with reference to FIGS. 1 and 2, generator 200 is configured to both supply and control the supply of energy to end effector assembly 100 of forceps 10 for treating tissue, and to provide feedback with respect to parameters of the tissue and/or energy during tissue treatment to enable a determination of the type of tissue being treated. Generator 200 generally includes a main controller 210, a high voltage DC power supply (HVPS) 220 (or other suitable power supply), an RF output stage 230 (or other suitable output depending on the energy delivered to end effector assembly 100), sensor circuitry 240, a machine learning unit 260, and a user interface 280, e.g., a graphical user interface to enable the input and display of a variety of information such as settings, warnings, treatment complete indicators, etc.

Main controller 210 includes a microprocessor 212 connected to a computer-readable storage medium or memory 214, which may be a volatile type memory, e.g., RAM, or a non-volatile type memory, e.g., flash media, disk media, etc. Main controller 210 is coupled to power supply 220 and/or RF output stage 230, thus allowing microprocessor 212 to control the output of energy from generator 200 to end effector assembly 100. In particular, power supply 220 and RF output stage 230, based on control signals received from microprocessor 212 and/or user input, e.g., activation of activation switch 92, cooperate to selectively provide energy to tissue-contacting plates 114, 124 of jaw members 110, 120 of end effector assembly 100 via electrical leads 9a, 9b to treat tissue grasped between jaw members 110, 120. Microprocessor 212 is further coupled to sensor circuitry 240 for receiving feedback signals from end effector assembly 100 to perform feedback-based control of the delivery of energy to forceps 10, as detailed below. Memory 214 may store suitable instructions, to be executed by microprocessor 212, for indicating the sequence, duration, and/or parameters associated with the energy delivery from generator 200 to end effector assembly 100 to treat tissue. In some embodiments, generator 200 is configured to supply energy to end effector assembly 100 according to a tissue sealing algorithm such that the supply of energy, together with the mechanical parameters of end effector assembly 100, e.g., pressure applied to tissue and the gap distance between tissue-contacting plates 114, 124, enable the sealing of tissue grasped between jaw members 110, 120. However, other suitable tissue treatment effects are also contemplated.

Sensor circuitry 240 includes suitable sensor components for measuring and providing feedback with respect to a variety of tissue and/or energy parameters. In particular, sensory circuitry 240 is coupled to electrical leads 9a, 9b for sensing one or more properties of tissue grasped between jaw members 110, 120 or the energy conducted therethrough during tissue treatment and for providing the same to machine learning unit 260. Sensor circuitry 240, for example, may be configured to sense the impedance of tissue grasped between jaw members 110, 120 during the conduction of energy between tissue-contacting plates 114, 124 and/or to sense power during the conduction of energy between tissue-contacting plates 114, 124. Exemplary embodiments utilizing impedance-sensing during tissue treatment are described in U.S. Patent Application Pub. Nos. 2012/0283731 and 2013/0041367, and U.S. Pat. No. 8,034,049, the entire contents of each of which are incorporated by reference herein. Sensory circuitry 240 relays the sensed data, e.g., impedance and power data, to machine learning unit 260.

Machine learning unit 260 includes a microprocessor 262 connected to a computer-readable storage medium or memory 264, which may be a volatile type memory, e.g., RAM, or a non-volatile type memory, e.g., flash media, disk media, etc. Memory 264 stores suitable instructions, to be executed by microprocessor 262, for receiving the sensed data from sensory circuitry 240, accessing storage device 266 of machine learning unit 260, determining a tissue typed based upon the sensed data and information stored in storage device 266, and providing feedback to main controller 210 based upon the determined tissue type. Although illustrated as part of generator 200, it is also contemplated that machine learning unit 260 be remote from generator 200, e.g., on a remote server, and accessible by generator 200 via a wired or wireless connection. In embodiments where machine learning unit 260 is remote, it is contemplated that machine learning unit 260 may be accessible by and connected to multiple generators 200.

Storage device 266 of machine learning unit 260 stores one or more machine learning applications, e.g., algorithms and/or models, configured to determine a tissue type based upon the sensed data received from sensory circuitry 240. The machine learning application(s) are trained on and learn from experimental data and/or data from previous procedures initially input into the one or more machine learning applications in order to enable the machine learning application(s) to identify tissue type based upon such types of data. Such data may include tissue impedance data, power data, and/or any other suitable data. Suitable machine learning applications include, for example, Support Vector Machines (SVMs), applications employing Principle Component Analysis, Hidden Markov Models (HMMs), applications employing the Monte Carlo Method, etc.

Machine learning applications are advantageous for use in determining tissue type at least in that complex sensor components and pre-defined categorization rules and/or algorithms are not required. Rather, machine learning applications utilizes the initially input data, e.g., the previous procedure data and/or experimental data, to determine statistical features and/or correlations that enable the determination of tissue type of unknown tissues by analyzing data therefrom. Thus, with the one or more machine learning applications having been trained as detailed above, such can be used to determine a type of tissue being treated using end effector assembly 100. More specifically, microprocessor 262 of machine learning unit 260 is configured, in response to receiving sensed data from sensory circuitry 240, to input the sensed data into the machine learning application(s) stored in storage device 266 in order to determine a tissue type of the tissue being treated using end effector assembly 100.

Once the tissue type is determined by machine learning unit 260, this information is relayed to main controller 210. Upon receipt of the tissue type information, depending upon the tissue type, settings, user input, etc., main controller 210 may output an alert and/or warning to user interface 280, implement a particular energy-delivery algorithm based upon which HVPS 220 and RF output stage 230 provide energy to end effector assembly 100, and/or inhibit further energy delivery to end effector assembly 100. This feedback-based control is described in more detailed below with reference to FIG. 4.

Figure 3A:
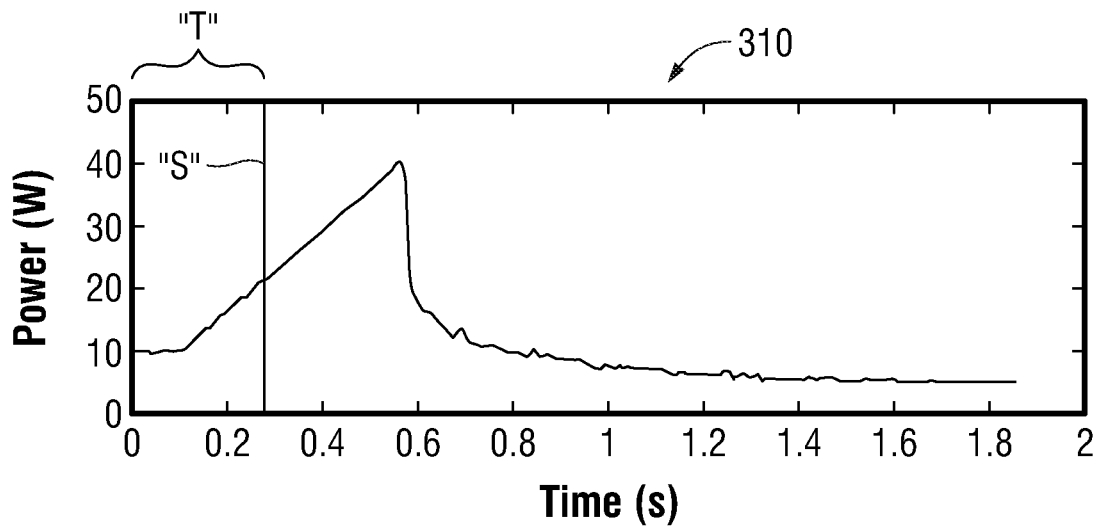
FIG. 3A is an exemplary power versus time graph during the course of treatment of tissue using the surgical system of FIG. 1.
Figure 3B:
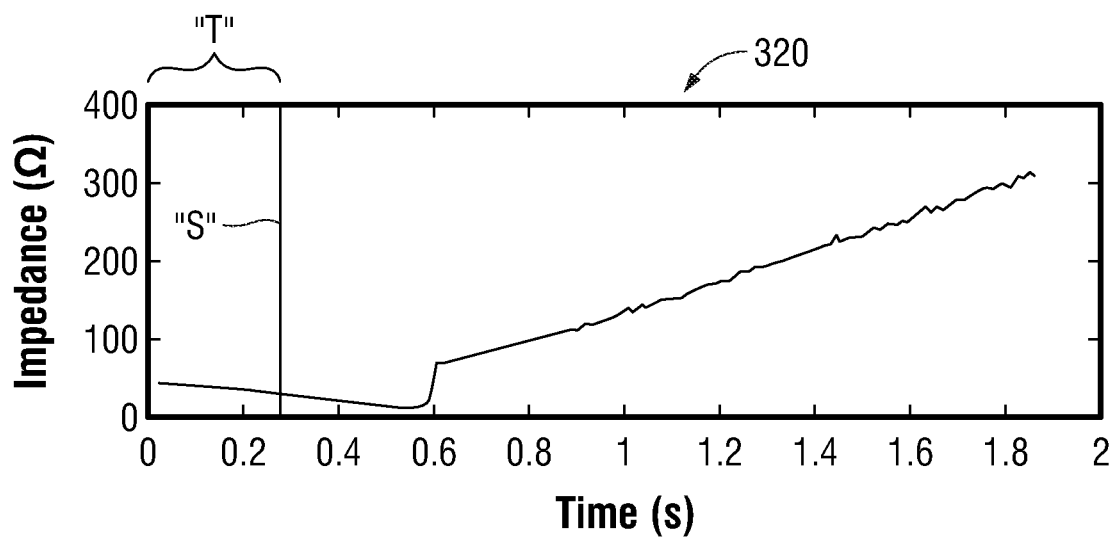
FIG. 3B is an exemplary impedance versus time graph during the course of treatment of tissue using the surgical system of FIG. 1.

Referring to FIGS. 3A and 3B, in conjunction with FIG. 2, as noted above, the data sensed by sensory circuitry 240 and utilized by machine learning unit 260 may include, for example, impedance data and/or power data. Exemplary graphs of power versus tissue treatment time 310 and impedance versus tissue treatment time 320 are illustrated in FIGS. 3A and 3B, respectively. The data formulating these graphs 310, 320 serves as a footprint of the tissue being treated. More specifically, it has been found that different tissue types result in different impedance data and/or power data. Further, it has been found that sufficient data to determine tissue type, when used with a machine leaning application, can be collected during the first 250 ms of tissue treatment. This is advantageous in that, although energy is being conducted between jaw members 110, 120 and through tissue, the first 250 ms of tissue treatment is a sufficiently short period of time so as not to permanently damage tissue. Accordingly, by sampling impedance and/or power data during the first 250 ms of tissue treatment and inputting this data into the machine learning application(s), a type of tissue grasped between jaw members 110, 120 can be determined before permanent tissue damage occurs. The impedance data and/or power data may be sampled as "snapshot" data, or data at a particular point in time during tissue treatment, e.g., at point "S," corresponding to 250 ms of elapsed tissue treatment time. Additionally or alternatively, the impedance data and/or power data may be sampled over a period of time during tissue treatment, e.g., period of time "T," spanning from the initiation of tissue treatment (time=0) to 250 ms of elapsed tissue treatment time. The graphs illustrated in FIGS. 3A and 3B, as noted above, are exemplary, and are only meant to illustrate the variation of power and impedance, respectively, during the course of tissue treatment. These graphs are not meant to be representative of any particular tissue type.

Figure 4:
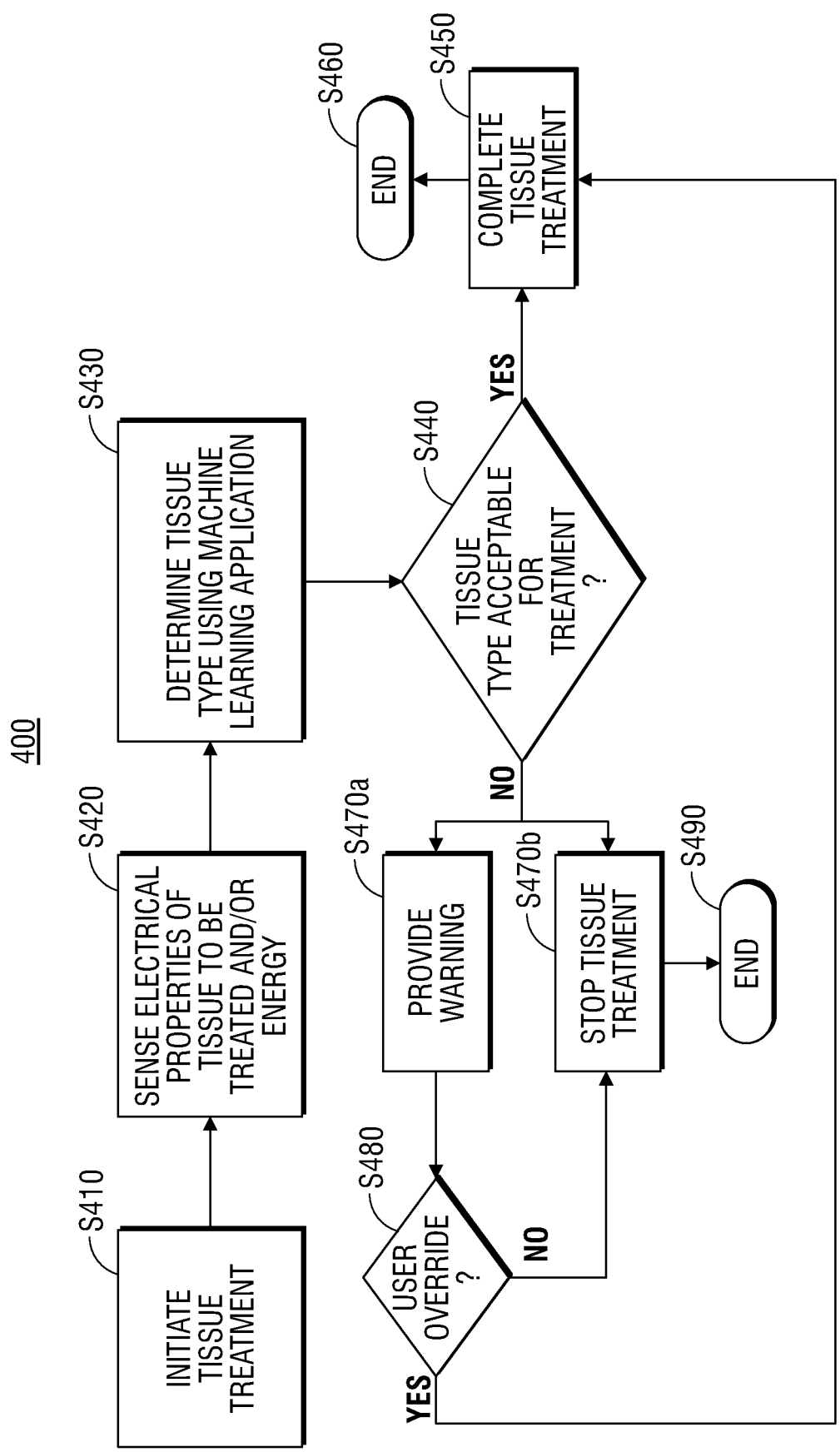
FIG. 4 is a flow diagram illustrating a process provided in accordance with the present disclosure.

Turning to FIG. 4, in conjunction with FIGS. 1 and 2, the use and operation of surgical system 1000 is detailed with respect to process 400. At S410, tissue treatment is initiated. Prior to initiation of tissue treatment, end effector assembly 100 is manipulated into position such that a target tissue to be treated is disposed between jaw members 110, 120, with jaw members 110, 120 in the spaced-apart position. Thereafter, movable handle 40 is compressed towards fixed handle 50 to pivot jaw members 110, 120 from the spaced-apart position to the approximated position to grasp tissue between plates 114, 124. With tissue grasped between plates 114, 124 of jaw members 110, 120, tissue treatment is initiated at S410 by activating activation switch 92 of activation assembly 90. As noted above, activating activation switch 92 initiates the supply of energy from generator 200 to plates 114, 124 via electrical leads 9a, 9b, such that energy is conducted through tissue grasped between plates 114, 124 to begin tissue treatment.

During tissue treatment, as indicated at S420, sensor circuitry 240 senses parameters of tissue and/or energy such as, for example, impedance and power. As noted above, this may occur as a snapshot "S" (FIGS. 3A and 3B) or over a time interval "T" (FIGS. 3A and 3B) and is determined at the beginning of tissue treatment, e.g., at or within 250 ms of tissue treatment, to avoid permanent damage to tissue should it be determined that treatment should be discontinued. As also noted above, the sensed data obtained by sensor circuitry 240 is relayed to machine learning unit 260.

As indicated at S430, machine learning unit 260, based upon the sensed data received from sensor circuitry 240, determines a tissue type using the machine learning application(s) stored in storage device 266 of machine learning unit 260. The determined tissue type is relayed to main controller 210, wherein a determination is made, at S440, as to whether the determined tissue type is one that is appropriate for the tissue treatment that has begun.

If the determined tissue type is acceptable for the tissue treatment that has begun ("YES" at S440), the process proceeds to S450, wherein tissue treatment is completed. An acceptable tissue type may include, for example, tissue determined to be vascular tissue, tissue determined to be nerveless (or include a minimal amount of nerve structures), tissue grouped into a category "A," etc. Completion of tissue treatment may include implementing (or continuing) a particular energy-delivery algorithm based upon which HVPS 220 and RF output stage 230 provide energy to end effector assembly 100 to fully treat the tissue grasped therebetween. In embodiments, the energy-delivery algorithm is pre-determined and applied once it is determined that the determined tissue type is acceptable for tissue treatment ("YES" at S440). In other embodiments, an energy-deliver algorithm is implemented or refined based upon the determined tissue type (after the tissue type is determined to be acceptable for treatment). Once tissue treatment is complete (S450), if desired, trigger 62 of trigger assembly 60 may be actuated to advance the knife through knife channels 125 and between jaw members 110, 120 to cut the treated tissue grasped therebetween. The process ends at S460, wherein tissue has been treated and, if desired, cut.

If the determined tissue type is found not to be acceptable for the tissue treatment that has begun ("NO" in S440), main controller 210 is configured to output a warning to the user at S470a, e.g., via user interface 280, and/or to stop further tissue treatment at S470b, e.g., inhibit further energy delivery to end effector assembly 100. A tissue type found to be unacceptable may include, for example, tissue determined to be non-vascular tissue, tissue determined to include nerves, organ tissue, tissue grouped into a category "B," etc.

The warning provided at S470a may be in the form of a visual warning displayed on user interface 280, an audible tone output by generator 200, and/or any other suitable warning. As indicated at S480, the warning provided at S470a may be manually overridden by the user ("YES" at S480), e.g., by clearing the warning from user interface 280, re-pressing activation switch 92, maintaining activation of activation switch 92 for a defined period of time, or in any other suitable matter. As an alternative to requiring a manual override, the override may be the default condition and, thus, the user must take action to prevent the override from automatically occurring, e.g., via releasing activation switch 92, confirming the warning on user interface 280, or in any other suitable manner. Where the override is accomplished ("YES" at S480), the process proceeds to S450, wherein tissue treatment is completed as detailed above and the process ends at S460, as also detailed above.

Where there is no override ("NO" at S480) or where the determination of an unacceptable tissue type results in the stoppage of further tissue treatment (S470*b*), the process ends at S490 without permitting further treatment of tissue. As such, the unacceptable tissue type is inhibited from being treated to the point where permanent damage may occur.

The above-detailed system 1000 and process 400 for enabling tissue type determination may be facilitated by the use of additional information in the machine learning application(s). For example, contextual information input into generator 200 (and provided to machine learning unit 260) such as the anatomical location of the tissue to be treated, patient data and patient condition information, data obtained from other sensors, e.g., optical tissue sensors, historical data relating to the determined tissue type of other tissues treated during the same procedure and/or previous similar procedures, information relating to manual overrides and non-overrides from previous procedures, etc., may allow for a more-refined determination of tissue type using the machine learning application(s) of machine learning unit 260.

The various embodiments disclosed hereinabove are particularly advantageous for use with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theatre or located in a remote location. In this instance, one team of surgeons or nurses may prep the patient for surgery and configure the robotic surgical system while another surgeon (or group of surgeons) remotely controls the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument, e.g., end effector assembly 100 of forceps 10 (with or without housing 20 and shaft 12). The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions. In particular, the robotic system may operably communicate with generator 200 such that the so-called "manual" operations of end effector assembly 100 may be performed via the robotic system (instead of handle assembly 30, trigger assembly 60, rotation assembly 70, activation assembly 90, etc.) and/or under control of generator 200. Alternatively, the robotic system may be fully integrated with generator 200 such that a fully automatic surgical procedure may be affected, under the guidance and/or selectively control of a remote surgeon.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of surgery, comprising:
   grasping tissue, between a first jaw member and a second jaw member of a surgical instrument;
   conducting energy through the grasped tissue;
   sensing at least one of impedance or power during the conduction of energy through the grasped tissue; and
   running at least one machine learning application to determine a type of the grasped tissue based upon the at least one of sensed impedance or sensed power, and based upon at least one of an anatomical location of the grasped tissue, patient condition information, or data obtained from an optical tissue sensor.

2. The method according to claim 1, further comprising determining whether the determined type of the grasped tissue is acceptable for tissue treatment or is not acceptable for tissue treatment.

3. The method according to claim 2, wherein, if it is determined that the determined type of grasped tissue is acceptable for tissue treatment, the method further includes continuing to conduct energy through the grasped tissue to complete tissue treatment.

4. The method according to claim 2, wherein, if it is determined that the determined type of grasped tissue is not acceptable for tissue treatment, the method further includes at least one of stopping the conduction of energy through the grasped tissue or outputting a warning.

5. The method according to claim 2, wherein determining whether the determined type of the grasped tissue is acceptable for tissue treatment or is not acceptable for tissue treatment is performed during an initial 250 ms of the conduction of energy through the grasped tissue.

6. The method according to claim 1, wherein the type of the grasped tissue is determined by the at least one machine learning application based upon, in part, a snapshot in time of at least one of impedance or power during the conduction of energy through the grasped tissue or based upon at least one of impedance or power over an elapsed time during the conduction of energy through the grasped tissue.

7. The method according to claim 1, further comprising communicating the determined type of the grasped tissue to a main controller configured to control the energy output of a generator.

8. The method according to claim 7, wherein the main controller is configured to determine whether the determined tissue type is acceptable for tissue treatment or not acceptable for tissue treatment during an initial stage of tissue treatment prior to permanently damaging tissue.

9. The method according to claim 8, wherein, if the determined tissue type is determined to be acceptable for tissue treatment, the method further comprises controlling a supply of energy to electrically-conductive plates of the first jaw member and the second jaw member to complete tissue treatment.

10. The method according to claim 7, wherein the at least one machine learning application is stored remotely from the generator.

11. The method according to claim 7, wherein the at least one machine learning application is stored within the generator.

12. The method according to claim 1, wherein the at least one machine learning application receives, as an input, sensed power data from sensor circuitry.

13. The method according to claim 1, wherein the at least one machine learning application is further configured to determine a type of tissue grasped between the first and second jaw members based on information relating to manual overrides.

14. The method according to claim 1, wherein the at least one machine learning application includes a Support Vector Machine (SVM), implements Principle Component Analysis, implements a Hidden Markov Model (HMM), or employs a Monte Carlo Method.

15. A non-transitory computer-readable storage medium in which is stored instructions for causing a processor to execute a computer-implemented method, the method comprising:
   conducting energy through grasped tissue, wherein the tissue is grasped between a first jaw member and a second jaw member of a surgical instrument;
   sensing, by a sensor, at least one of impedance or power during the conduction of energy through the grasped tissue; and
   determining by at least one machine learning application a type of the grasped tissue based upon the at least one of sensed impedance or sensed power, and based upon at least one of an anatomical location of the grasped tissue, patient condition information, or data obtained from an optical tissue sensor.

16. The method non-transitory computer-readable storage medium according to claim 15, the computer-implemented method further comprising determining whether the determined type of the grasped tissue is acceptable for tissue treatment or is not acceptable for tissue treatment.

17. The non-transitory computer-readable storage medium according to claim 16, wherein, if it is determined that the determined type of grasped tissue is acceptable for tissue treatment, the method further includes continuing to conduct energy through the grasped tissue to complete tissue treatment.

18. The non-transitory computer-readable storage medium according to claim 16, wherein, if it is determined that the determined type of grasped tissue is not acceptable for tissue treatment, the method further includes at least one of stopping the conduction of energy through the grasped tissue or outputting a warning.

19. The non-transitory computer-readable storage medium according to claim 16, wherein determining whether the determined type of the grasped tissue is acceptable for tissue treatment or is not acceptable for tissue treatment is performed during an initial 250 ms of the conduction of energy through the grasped tissue.

\* \* \* \* \*